(12) United States Patent
Oganesian

(10) Patent No.: US 6,779,525 B1
(45) Date of Patent: Aug. 24, 2004

(54) TRACHEOTOMY STOMA COVERING DEVICE

(76) Inventor: Niko Oganesian, 7803 Alderdale St., Downey, CA (US) 90240

( * ) Notice: Subject to any disclaimer, the term of this patent is extended or adjusted under 35 U.S.C. 154(b) by 293 days.

(21) Appl. No.: 09/961,733

(22) Filed: Sep. 24, 2001

(51) Int. Cl.[7] ............................................. A61M 16/00
(52) U.S. Cl. ............................ 128/207.17; 128/207.14
(58) Field of Search ...................... 128/200.26, 207.14, 128/207.15, 207.17, 909, 918, 200.24, 888, DIG. 26; 604/308, 332, 337, 338

(56) References Cited

U.S. PATENT DOCUMENTS

| | | | | |
|---|---|---|---|---|
| 3,811,436 A | * | 5/1974 | Ferrell | 128/205.29 |
| 3,920,009 A | * | 11/1975 | Olsen | 128/201.13 |
| 4,463,757 A | * | 8/1984 | Schmidt | 128/205.29 |
| 5,022,394 A | * | 6/1991 | Chmielinski | 128/207.14 |
| 5,042,468 A | * | 8/1991 | Lambert | 128/200.26 |
| 5,058,579 A | * | 10/1991 | Terry et al. | 128/207.14 |
| 5,445,145 A | * | 8/1995 | Redmon | 128/207.16 |
| 5,616,116 A | * | 4/1997 | Born | 600/32 |
| 5,840,091 A | * | 11/1998 | Strong | 55/385.1 |
| 5,848,590 A | * | 12/1998 | Smith | 128/201.13 |
| 6,186,139 B1 | * | 2/2001 | Bezicot et al. | 128/200.24 |
| D461,896 S | * | 8/2002 | Worthington | D24/162 |
| 2003/0029456 A1 | * | 2/2003 | Lambert | 128/207.15 |

* cited by examiner

Primary Examiner—Teena Mitchell
(74) Attorney, Agent, or Firm—Goldstein Law Offices, P.C.

(57) ABSTRACT

A tracheotomy stoma covering device including a cover member dimensioned for being positioned over a tracheotomy stoma of a person. A gauze member is adapted for coupling with the cover member for covering the tracheotomy stoma of the person. A pair of strap members are positionable around the person's neck for engaging the cover member.

2 Claims, 4 Drawing Sheets

TRACHEOTOMY STOMA COVERING DEVICE

BACKGROUND OF THE INVENTION

The present invention relates to a tracheotomy stoma covering device and more particularly pertains to keeping a stoma on a person's throat closed to allow normal functions and prevent infection.

The use of medical devices is known in the prior art. More specifically, medical devices heretofore devised and utilized for the purpose of facilitating healthy living are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,463,757 to Schmidt discloses a covering device for a tracheotomy stoma comprised of a flexible mesh panel attached to the wearer's neck with a strap for providing filtering and conditioning to the air. U.S. Pat. No. 3,811,436 to Ferrell and U.S. Pat. No. 6,186,139 to Bezicot disclose stoma filter assemblies that are attached to the neck of a patient.

While these devices fulfill their respective, particular objective and requirements, the aforementioned patents do not describe a tracheotomy stoma covering device for keeping a stoma on a person's throat closed to allow normal functions and prevent infection.

In this respect, the tracheotomy stoma covering device according to the present invention substantially departs from the conventional concepts and designs of the prior art, and in doing so provides an apparatus primarily developed for the purpose of keeping a stoma on a person's throat closed to allow normal functions and prevent infection.

Therefore, it can be appreciated that there exists a continuing need for a new and improved tracheotomy stoma covering device which can be used for keeping a stoma on a person's throat closed to allow normal functions and prevent infection. In this regard, the present invention substantially fulfills this need.

SUMMARY OF THE INVENTION

In the view of the foregoing disadvantages inherent in the known types of medical devices now present in the prior art, the present invention provides an improved tracheotomy stoma covering device. As such, the general purpose of the present invention, which will be described subsequently in greater detail, is to provide a new and improved tracheotomy stoma covering device which has all the advantages of the prior art and none of the disadvantages.

To attain this, the present invention essentially comprises a cover member dimensioned for being positioned over a tracheotomy stoma of a person. The cover member has an upper edge, a lower edge, opposed side edges, an inner surface and an outer surface. The opposed side edges each have a pair of straps extending laterally therefrom. The straps each have free ends. The straps each have a slot therethrough inwardly of the free ends thereof. The inner surface has a hook and loop patch disposed thereon. A gauze member is adapted for coupling with the cover member for covering the tracheotomy stoma of the person. The gauze member has an inner surface and an outer surface. The outer surface of the gauze member has a hook and loop patch disposed thereon for engaging the hook and loop patch disposed on the inner surface of the cover member. A pair of strap members are positionable around the person's neck for engaging the cover member. The pair of strap members each have a main central section. The main central section has extensions extending outwardly of opposed free ends thereof in a co-linear relationship. The extensions have narrow strips extending outwardly from free ends thereof in a co-linear relationship. The extensions and the narrow strips each have hook and loop patches disposed thereon. The narrow strips are positionable through the slots of the straps of the cover member and then can be folded back against the extensions whereby the hook and loop patches of the extensions and narrow strips couple.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tracheotomy stoma covering device which has all the advantages of the prior art medical devices and none of the disadvantages.

It is another object of the present invention to provide a new and improved tracheotomy stoma covering device which may be easily and efficiently manufactured and marketed.

It is a further object of the present invention to provide a new and improved tracheotomy stoma covering device which is of durable and reliable construction.

An even further object of the present invention is to provide a new and improved tracheotomy stoma covering device which is susceptible of a low cost of manufacture with regard to both materials and labor, and which accordingly is then susceptible of low prices of sale to the consuming public, thereby making such a tracheotomy stoma covering device economically available to the buying public.

Even still another object of the present invention is to provide a new and improved tracheotomy stoma covering device for keeping a stoma on a person's throat closed to allow normal functions and prevent infection.

Lastly, it is an object of the present invention to provide a new and improved tracheotomy stoma covering device including a cover member dimensioned for being positioned over a tracheotomy stoma of a person. A gauze member is adapted for coupling with the cover member for covering the tracheotomy stoma of the person. A pair of strap members are positionable around the person's neck for engaging the cover member.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
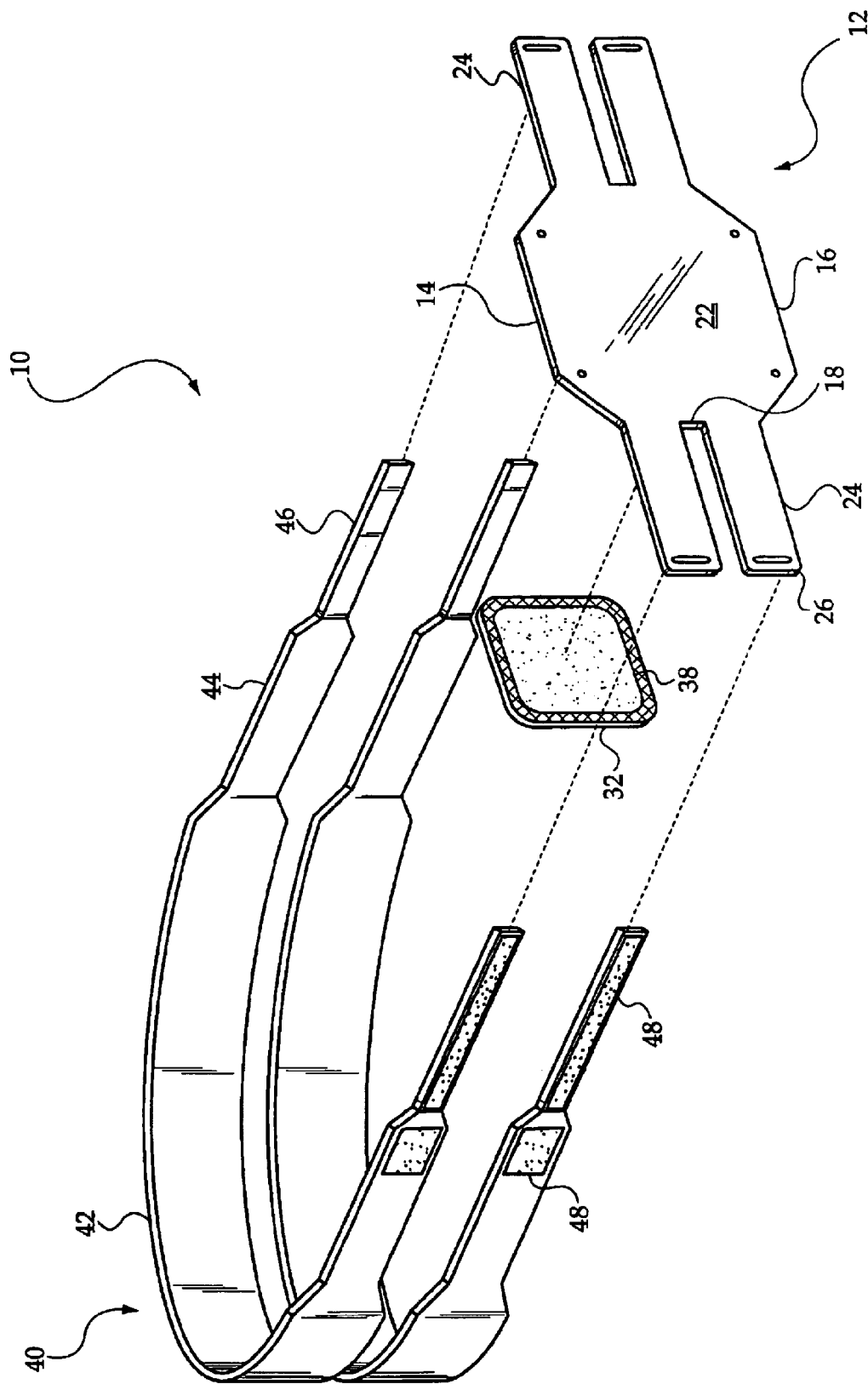
FIG. 1 is a perspective view of the preferred embodiment of the tracheotomy stoma covering device constructed in accordance with the principles of the present invention.
Figure 2:
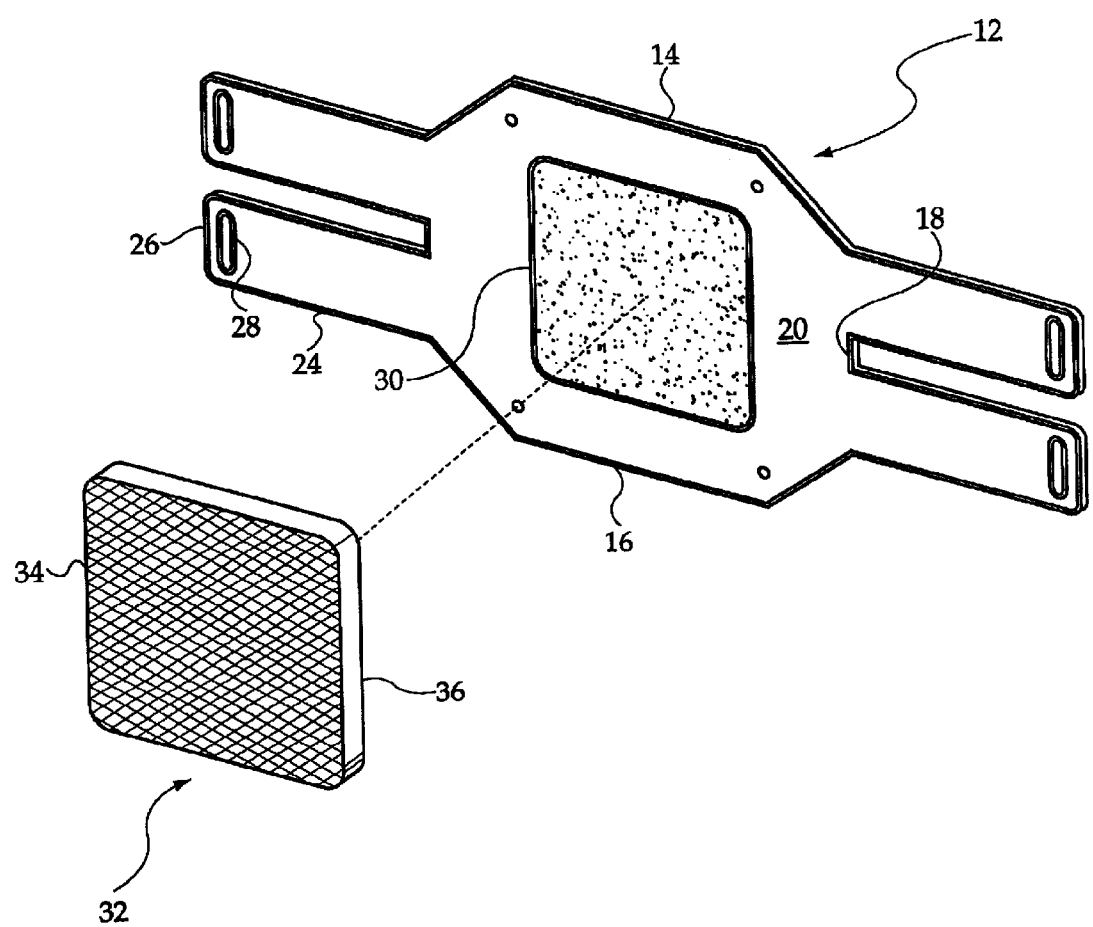
FIG. 2 is a rear perspective view of the cover member and the gauze member of the present invention.
Figure 3:
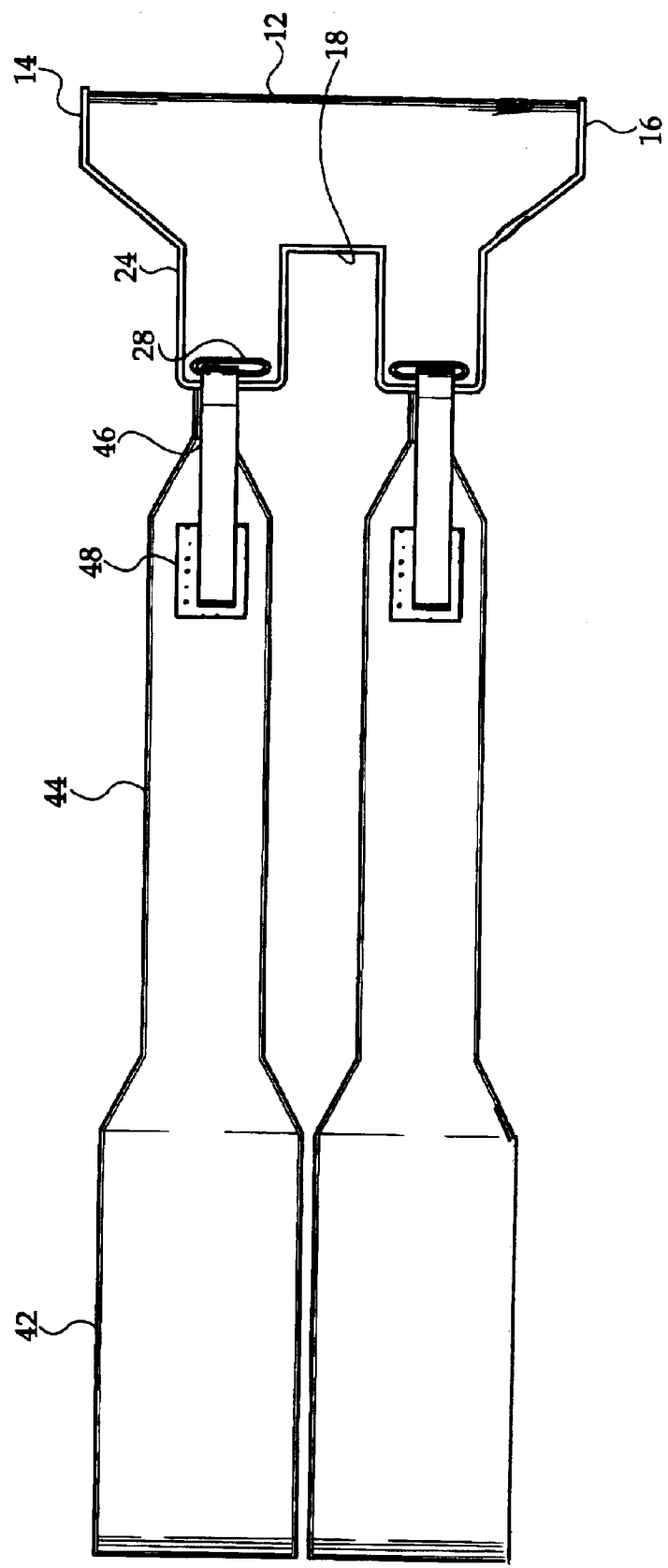
FIG. 3 is a side elevation view of the present invention.
Figure 4:
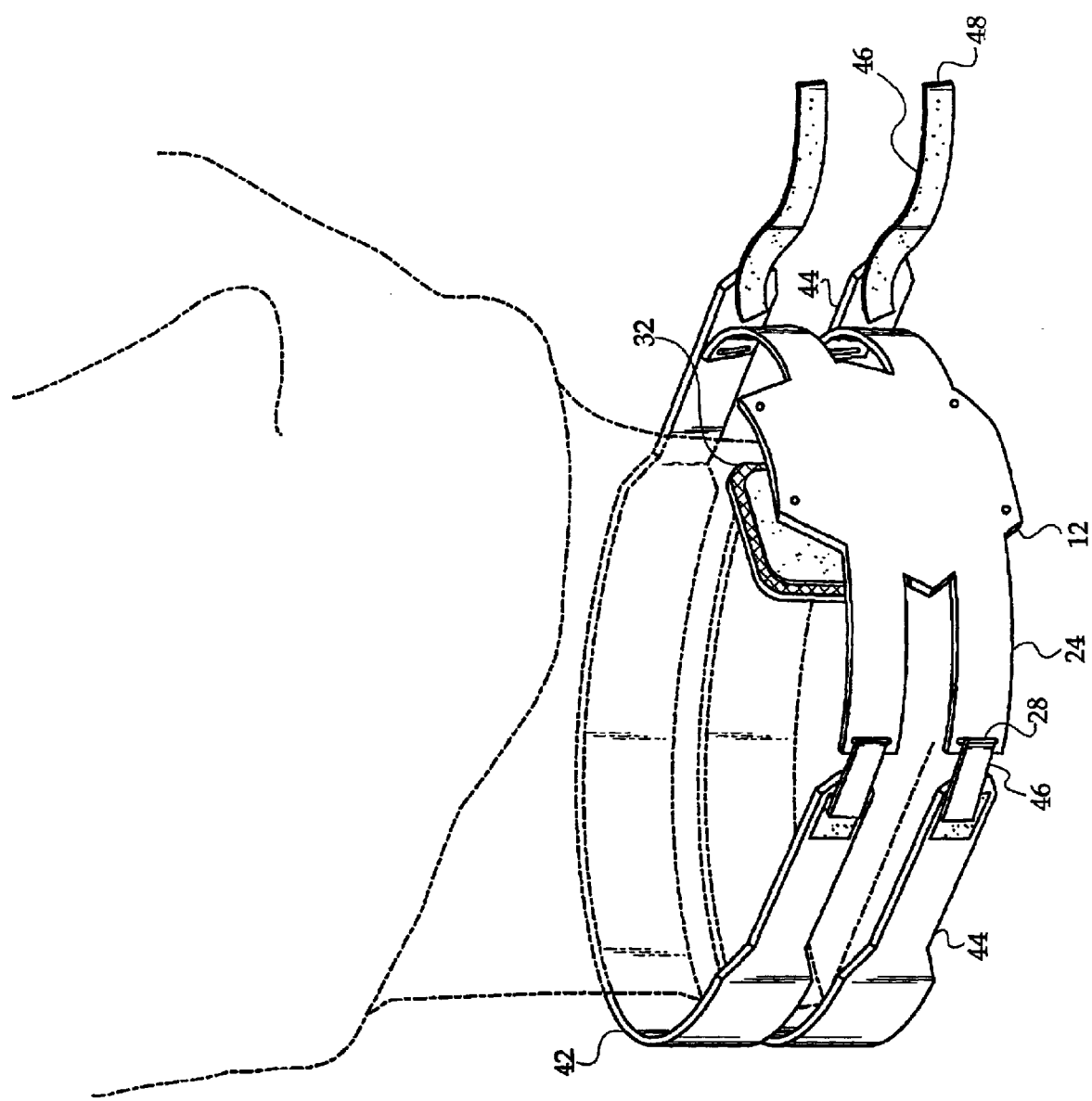
FIG. 4 is a perspective view of the present invention illustrated in use.

With reference now to the drawings, and in particular, to FIGS. 1 through 4 thereof, the preferred embodiment of the new and improved tracheotomy stoma covering device embodying the principles and concepts of the present invention and generally designated by the reference number 10 will be described.

Specifically, it will be noted in the various Figures that the device relates to a tracheotomy stoma covering device for keeping a stoma on a person's throat closed to allow normal functions and prevent infection. In its broadest context, the device consists of a cover member, a gauze member, and a pair of strap members. Such components are individually configured and correlated with respect to each other so as to attain the desired objective.

The cover member 12 is dimensioned for being positioned over a tracheotomy stoma of a person. The cover member 12 has an upper edge 14, a lower edge 16, opposed side edges 18, an inner surface 20 and an outer surface 22. The opposed side edges 18 each have a pair of straps 24 extending laterally therefrom. The straps 24 each have free ends 26. The straps 24 each have a slot 28 therethrough inwardly of the free ends 26 thereof. The inner surface 20 has a hook and loop patch 30 disposed thereon.

The gauze member 32 is adapted for coupling with the cover member 12 for covering the tracheotomy stoma of the person. The gauze member 32 has an inner surface 34 and an outer surface 36. The outer surface 36 of the gauze member 32 has a hook and loop patch 38 disposed thereon for engaging the hook and loop patch 30 disposed on the inner surface 20 of the cover member 12.

The pair of strap members 40 are positionable around the person's neck for engaging the cover member 12. The pair of strap members 40 each have a main central section 42. The main central section 42 has extensions 44 extending outwardly of opposed free ends thereof in a co-linear relationship. The extensions 44 have narrow strips 46 extending outwardly from free ends thereof in a co-linear relationship. The extensions 44 and the narrow strips 46 each have hook and loop patches 48 disposed thereon. The narrow strips 46 are positionable through the slot's 28 of the strap's 24 of the cover member 12 and then can be folded back against the extensions 48 whereby the hook and loop patches 48 of the extensions 44 and narrow strips 46 couple.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed is:

1. A tracheotomy stoma covering device for keeping a stoma on a person's throat closed to allow normal functions and prevent infection comprising, in combination:

a cover member dimensioned for being positioned over a tracheotomy stoma of a person, the cover member having an upper edge, a lower edge, opposed side edges, an inner surface and an outer surface, the opposed side edges each having a pair of straps extending laterally therefrom, the straps each having free ends, the straps each having a slot therethrough inwardly of the free ends thereof, the inner surface having a hook and loop patch disposed thereon;

a gauze member adapted for coupling with the cover member for covering the tracheotomy stoma of the person, the gauze member having an inner surface and an outer surface, the outer surface of the gauze member having a hook and loop patch disposed thereon for engaging the hook and loop patch disposed on the inner surface of the cover member; and a pair of strap members positionable around the person's neck for engaging the cover member, the pair of strap members each having a main central section, the main central section having extensions extending outwardly of opposed free ends thereof in a co-linear relationship, the extensions having narrow strips extending outwardly from free ends thereof in a co-linear relationship, the extensions and the narrow strips each having hook and loop patches disposed thereon, the narrow strips being positionable through the slots of the straps of the cover member and then folded back against the extensions whereby the hook and loop patches of the extensions and narrow strips couple.

2. A tracheotomy stoma covering device for keeping a stoma on a person's throat closed to allow normal functions and prevent infection comprising, in combination:

a cover member dimensioned for being positioned over a tracheotomy stoma of a person, the cover member having an upper edge, a lower edge, opposed side edges, an inner surface and an outer surface, the opposed side edges each having a pair of straps extending laterally therefrom;

a gauze member adapted for coupling with the cover member for covering the tracheotomy stoma of the person;

a pair of strap members positionable around the person's neck for engaging the cover member; and wherein the pair of strap members each have a main central section, the main central section having extensions extending outwardly of opposed free ends thereof in a co-linear relationship, the extensions having narrow strips extending outwardly from free ends thereof in a co-linear relationship, the extensions and the narrow strips each having hook and loop patches disposed thereon, the narrow strips being positionable through slots in the cover member and then folded back against the extensions whereby the hook and loop patches of the extensions and narrow strips couple.

* * * * *